United States Patent [19]
Imai et al.

[11] 4,339,615
[45] Jul. 13, 1982

[54] PROCESS FOR PRODUCING RESORCINOL

[75] Inventors: Ichiro Imai, Funabashi; Fujihisa Matsunaga; Hiroaki Nakagawa, both of Iwakuni; Masayasu Isibasi, Waki; Tohru Taguchi, Ichihara, all of Japan

[73] Assignee: Mitsui Petrochemical Industries Ltd., Tokyo, Japan

[21] Appl. No.: 205,182

[22] Filed: Nov. 10, 1980

[30] Foreign Application Priority Data

Nov. 12, 1979 [JP] Japan .............................. 54/145360

[51] Int. Cl.³ ...................... C07C 37/08; C07C 39/08
[52] U.S. Cl. .................................... 568/768; 568/798
[58] Field of Search .............................. 568/768, 798

[56] References Cited

U.S. PATENT DOCUMENTS 3,376,352 4/1968 Domenicali et al. ............... 568/768
3,798,277 3/1974 Masatoshi et al. .................. 568/768
4,112,243 9/1978 Nowak et al. ...................... 568/768

FOREIGN PATENT DOCUMENTS 743736 1/1956 United Kingdom ................ 568/768

Primary Examiner—Werren B. Lone
Attorney, Agent, or Firm—Sherman & Shalloway

[57] ABSTRACT

In a process for producing resorcinol, which comprises cleaving m-diisopropylbenzene dihydroperoxide in the presence of a water-soluble acid catalyst in a mixed solvent consisting of an aromatic hydrocarbon and acetone, treating the resulting acid cleavage product containing resorcinol with an aqueous solution of a neutral salt under acidic conditions, separating the solvent layer containing resorcinol from the aqueous layer, and recovering resorcinol from the separated solvent layer; the improvement wherein (i) the acid cleavage is carried out while maintaining the weight ratio of the aromatic hydrocarbon to acetone at less than 0.6, and at a time after formation of the acid cleavage product but before the treatment of the cleavage product with the aqueous solution of the neutral salt, the amount of the aromatic hydrocarbon in the mixed solvent is adjusted so that the weight ratio of the aromatic hydrocarbon to acetone in the product is from 0.6 to 1.1, and (ii) the acidic conditions are selected such that the pH of the solvent layer containing resorcinol is 2.5 to 4.

9 Claims, No Drawings

PROCESS FOR PRODUCING RESORCINOL

This invention relates to an improved process for producing resorcinol from m-diisopropylbenzene dihydroperoxide (to be abbreviated m-DHP). According to this process, resorcinol can be produced in high yields with commercial advantage while advantageously eliminating various troubles such as the undesirable increase of loads in a distillation operation and apparatus and the occurrence of plugging, contamination and corrosion of the apparatus. Moreover, the acid cleavage of m-DHP can be performed smoothly, and the acid catalyst can be efficiently removed from the resulting acid cleavage product of m-DHP.

A process has long been known for producing resorcinol from m-DHP which comprises the acid cleavage of m-DHP, the removal of the acid catalyst from the acid cleavage product by neutralization, the separation of the solvent layer from the aqueous layer, and the recovery of resorcinol from the solvent layer. A number of improvements of this process have also been proposed (for example, British Pat. Nos. 743,736 and 805,048).

The present invention relates to an improvement of this conventional process, and provides a new and improved process for producing resorcinol, which comprises cleaving m-diisopropylbenzene dihydroperoxide in the presence of a water-soluble acid catalyst in a mixed solvent consisting of an aromatic hydrocarbon and acetone, treating the resulting acid cleavage product containing resorcinol with an aqueous solution of a neutral salt under acidic conditions, separating the solvent layer containing resorcinol from the aqueous layer, and recovering resorcinol from the separated solvent layer.

In order to increase the overall yield of resorcinol in the production of resorcinol from m-DHP, not only the yield of resorcinol at the time of acid cleavage, but also a loss of resorcinol in a post-treating procedure such as distillation and the amount of resorcinol recovered at the time of thermal cracking of high-boiling by-products must be taken into consideration. However, there have been few cases in which the method of producing resorcinol has been studied from such an overall standpoint. Another problem with the production of resorcinol is that in neutralizing the acid catalyst, water or a metal salt derived from the alkali used in the neutralization tends to get mixed with the neutralization product. This consequently causes increased loads in distillation, and also causes plugging, contamination and corrosion of the apparatus.

The present inventors made extensive investigations in order to develop an improved process for producing resorcinol smoothly in high yields with commercial advantage by removing these troubles.

It has now been found in accordance with this invention that resorcinol can be prepared smoothly in high yields with commercial advantage from m-DHP while removing the aforesaid troubles of the prior art when the aforesaid process of this invention is carried out under a specified set of conditions (i) and (ii) mentioned below.

Specifically, the present invention provides a process for producing resorcinol, which comprises cleaving m-diisopropylbenzene dihydroperoxide in the presence of a water-soluble acid catalyst in a mixed solvent consisting of an aromatic hydrocarbon and acetone, treating the resulting acid cleavage product containing resorcinol with an aqueous solution of a neutral salt under acidic conditions, thereby separating the solvent layer containing resorcinol from the aqueous layer, and recovering resorcinol from the separated solvent layer; characterized in that (i) the acid cleavage is carried out while maintaining the weight ratio of the aromatic hydrocarbon to acetone at less than 0.6, and at a time after formation of the acid cleavage product but before the treatment of the cleavage product with the aqueous solution of the neutral salt, the amount of the aromatic hydrocarbon in the mixed solvent is adjusted so that the weight ratio of the aromatic hydrocarbon to acetone in the product is from 0.6 to 1.1, and (ii) the acidic conditions are selected such that the pH of the solvent layer containing resorcinol is 2.5 to 4.

The present invention is described below in greater detail.

As is well known, m-DHP can be produced by liquid-phase oxidation of m-diisopropylbenzene (to be abbreviated m-DIPB) and/or m-diisopropylbenzene monohydroperoxide (to be abbreviated m-MHP) with molecular oxygen such as air. Usually, this liquidphase oxidation product contains m-2-hydroxy-2-propyl-alpha,alphadimethylbenzylhydroperoxide (to be abbreviated m-HHP), m-di(2-hydroxy-2-propyl)benzene (to be abbreviated m-DC) and ketones in addition to m-DHP, m-MHP and m-DIPB. In the present invention, such an oxidation product itself, or a product obtained by oxidizing it with an oxidizing agent such as hydrogen peroxide to convert m-HHP or m-DC to m-DHP may be used as the starting m-DHP in the process of this invention. If desired, the unreacted material or by-products may be removed partly or wholly from the starting m-DHP before it is submitted to the process of this invention.

In the process of this invention, m-DHP is cleaved in the presence of a water-soluble acid catalyst in a mixed solvent composed of an aromatic hydrocarbon and acetone in which the weight ratio of the aromatic hydrocarbon to acetone is less than 0.6.

The acid catalyst and aromatic hydrocarbon may be those compounds which are known in the art, and the acid cleavage conditions may be those known in the art.

Examples of the acid catalyst are sulfuric acid, phosphoric acid and perchloric acid, and sulfuric acid is preferred. The aromatic hydrocarbon may, for example, be a $C_6$–$C_{12}$ aromatic hydrocarbon such as benzene, toluene, xylene, ethylbenzene, cumene, pseudocumene, cymene, diethylbenzene and DIPB.

The reaction temperature required in the acid cleavage is room temperature to about 110° C., for example about 30° C. to about 110° C., preferably about 50° to about 90° C. The reaction time (or residence time) is about 1 to about 60 minutes, preferably about 3 to about 20 minutes.

It is essential that in performing the acid cleavage in the process of this invention, the weight ratio of the aromatic hydrocarbon to acetone in the mixed solvent is adjusted to less than 0.6, preferably from 0.05 to 0.55, more preferably from about 0.1 to about 0.4. Acetone is formed also as a product of the acid cleavage reaction, and in the present invention, the amount of acetone in the acid cleavage step includes that of acetone formed by the acid cleavage reaction. Thus, for example, in the acid cleavage reaction carried out batchwise, the amount of acetone in the reaction product upon completion of the reaction should be within the weight ratio range specified above. In the continuous operation of the acid cleavage reaction, the amount of acetone in the reaction product continuously withdrawn from the reaction zone should be within the above specified weight ratio. If the weight ratio of the aromatic hydrocarbon to acetone exceeds 0.6 the yield of resorcinol decreases.

The amount of the mixed solvent consisting of an aromatic hydrocarbon and acetone may be selected properly. Preferably, it is such that the concentration of resorcinol in the resulting reaction product is about 3 to about 20% by weight. The amount of the acid catalyst can also be selected properly, and is preferably about 0.05 to about 1% by weight, more preferably about 0.05 to about 0.6% by weight.

The acid cleavage reaction product containing resorcinol is then rotated with an aqueous solution of a neutral salt under acidic conditions thereby to move the acid catalyst in the product to the aqueous layer. The weight ratio of the aromatic hydrocarbon to acetone in the mixed solvent is adjusted at a certain time after the formation of the acid cleavage product but before the treatment with the neutral salt so that the weight ratio of aromatic hydrocarbon/acetone in the product is from 0.6 to 1.1, preferably from 0.65 to 1.1. This adjustment can be effected by partly removing acetone, and/or supplying an additional amount of the aromatic hydrocarbon. The adjustment can be easily effected by supplying an additional amount of the aromatic hydrocarbon.

By adjusting the weight ratio of the aromatic hydrocarbon to acetone, both the amounts of the neutral salt and water which get mixed with the solvent layer containing resorcinol, and the amounts of acetone and resorcinol which get mixed with the aqueous layer can be decreased. Accordingly, in recovering resorcinol by a distillation means from the solvent layer separated from the aqueous layer it is possible to reduce distillation loads and to avoid advantageously troubles attributed to the inclusion of the neutral salt, such as the plugging, contamination and corrosion of the apparatus.

Examples of the neutral salt used to treat the acid cleavage product are sodium sulfate, potassium sulfate, sodium chloride and sodium phosphate. The sulfates are preferred.

The concentration of the neutral salt in the aqueous solution is not critical, and is, for example, about 5 to about 50% by weight, preferably about 5 to about 30% by weight, more preferably about 10 to about 25% by weight. The amount of the aqueous solution of the neutral salt can also be selected properly. For example, it is about 0.3 to about 2 parts by volume per part by volume of the acid cleavage product containing resorcinol. The treating temperature can also be selected properly, and for example, it is room temperature to about 70° C., for example, about 30° to about 70° C.

In combination with the condition (i), it is essential in the process of this invention that the acidic conditions in the above treatment should be selected such that the pH of the solvent layer containing resorcinol which is separated from the aqueous layer is 2.5 to 4, preferably 2.5 to 3.5. When the pH of the solvent layer exceeds 4, the yield of resorcinol in the thermal cracking of high-boiling by-products is reduced, and the amount of the neutral salt included in the solvent layer containing resorcinol increases. When the pH is less than 2.5, the amount of resorcinol lost tends to increase. Accordingly, the use of acidic conditions within the above pH range is preferred. Basic compounds such as sodium hydroxide, potassium hydroxide, and sodium carbonate may be added to the treating system to adjust the pH.

The pH of the solvent layer containing resorcinol denotes the pH of the aqueous layer which is obtained by collecting a certain volume of a sample from the solvent layer, adding the same volume of water to it, and shaking the mixture.

After performing the acid cleavage step and the step of treating the acid cleavage product with the aqueous solution of the neutral salt, the solvent layer containing resorcinol is separated from the aqueous layer of the treated product, and resorcinol is recovered from the separated solvent layer. The separating and recovering steps can be performed in the same way as in the prior art.

For example, when after treatment with the aqueous solution of the neutral salt, the product is allowed to stand, an aqueous layer and a solvent layer containing resorcinol form. Hence, the solvent layer can be easily separated from the aqueous layer. Since the aqueous layer is usually weakly acidic, a suitable amount of the above-exemplified basic compound may be added to it to use it again in the treatment of the acid cleavage product with the aqueous solution of the neutral salt under the acidic conditions. This may obviate the trouble of treating the waste water.

The recovery of resorcinol from the separated solvent layer can be performed by a known distillation means.

In the distillation step, it is possible to distil off acetone, water, aromatic hydrocarbons, etc. first, and then resorcinol. Thermal cracking of high-boiling fractions can afford resorcinol. Known techniques can be applied to the separation and recovery of resorcinol.

According to the process of this invention, resorcinol can be obtained in high yields, and troubles such as the contamination of the apparatus are reduced. The process can be continuously operated for a long period of time. Moreover, the acid catalyst can be removed from the resulting acid cleavage product of m-DHP with an increased efficiency.

The following Examples illustrate the present invention more specifically.

EXAMPLE 1

A material of the following composition and a catalyst solution on of the following formulation were continuously fed into a continuous acid-cleavage reactor.

| Composition of the starting material | |
|---|---|
| m-DHP | 174 parts by weight |
| m-MHP | 14 parts by weight |
| m-HHP | 7 parts by weight |
| Toluene | 93 parts by weight |
| Other organic compounds | 47 parts by weight |
| Water | 1.5 parts by weight |
| Formulation of the catalyst solution | |
| Sulfuric acid | 1.3 parts by weight |
| Water | 2.5 parts by weight |
| Acetone | 331 parts by weight |

The acid cleavage reaction was carried out at 67° C. for a residence time of 5 minutes. The reaction product continuously discharged from the reactor had the following composition.

| | |
|---|---|
| Resorcinol | 66 parts by weight |
| iso-Propylphenol | 9 parts by weight |
| Toluene | 93 parts by weight |
| Acetone | 426 parts by weight |
| Water | 6.7 parts by weight |
| Sulfuric acid | 1.3 parts by weight |
| Other organic compounds | 70 parts by weight |

In feeding the above reaction product to an acid extracting tank, 258 parts by weight of toluene, 940 parts by weight of a 20% aqueous solution of $Na_2SO_4$ and 4.4 parts by weight of a 25% aqueous solution of NaOH were added to it in a feed pipe. The acid extraction tank was maintained at 50° C., and was adapted to provide a residence time of 30 minutes. The solvent layer (ph 3.3) was isolated from the top of the acid extraction tank, and the individual components were distilled and high-boiling compounds were thermally cracked to recover resorcinol.

The amount of sodium component in the solvent layer was 10 ppm, and the amount of water therein was 6.6% by weight. The ratio of recovery of resorcinol was 86 mole % based on DHP in the starting material.

EXAMPLES 2 TO 9 AND COMPARATIVE EXAMPLES 1 TO 10

The procedure of Example 1 was repeated except that a starting material of each of the compositions shown in Table 1 was used, and the acid cleavage conditions were changed as shown in Table 1, and the extracting conditions were changed as shown in Table 2. The results are shown in Tables 1 and 2.

It is seen that when the toluene/acetone ratio at the time of extraction is lower than in the present invention (Comparative Examples 1, 4 and 7), the ratio of recovery of resorcinol is high, but the contents of sodium and water in the solvent layer are too large.

When the pH of the solvent layer withdrawn from the extraction tank is higher than that specified in the present invention (Comparative Examples 2 and 3), the ratio of recovery of resorcinol is low.

When the toluene/acetone ratio at the time of acid cleavage is higher than the upper limit in the present invention (Comparative Examples 5 and 6), the ratio of recovery of resorcinol is low.

When the toluene/acetone ratio at the time of acid cleavage, the toluene/acetone ratio at the time of extraction, and the pH of the solvent layer are adjusted to the ranges specified in this invention (Examples 1 to 9), the ratio of recovery of resorcinol is high, and the contents of water and the sodium content in the solvent layer are small. Hence, the distilling operation is easy and the process of this invention can be continuously operated for a long period of time.

TABLE 1

| Example (Ex.) or Comparative Example (CEx.) | Ex. 1 | CEx. 1 | CEx. 2 | CEx. 3 | CEx. 4 | CEx. 5 | Ex. 2 | Ex. 3 | Ex. 4 | CEx. 6 |
|---|---|---|---|---|---|---|---|---|---|---|
| Composition of the starting material (parts by weight) | | | | | | | | | | |
| m-DHP | 174 | 174 | 174 | 174 | 174 | 174 | 174 | 174 | 174 | 174 |
| m-MHP | 14 | 14 | 14 | 14 | 14 | 14 | 14 | 14 | 14 | 14 |
| m-HHP | 7 | 7 | 7 | 7 | 7 | 7 | 7 | 7 | 7 | 7 |
| Toluene | 93 | 93 | 93 | 93 | 93 | 237 | 93 | 160 | 160 | 160 |
| Other organic compounds | 47 | 47 | 47 | 47 | 47 | 47 | 47 | 47 | 47 | 47 |
| Water | 1.5 | 1.5 | 1.5 | 1.5 | 1.5 | 1.5 | 1.5 | 1.5 | 1.5 | 1.5 |
| Catalyst solution (parts by weight) | | | | | | | | | | |
| Sulfuric acid | 1.3 | 1.3 | 1.3 | 1.3 | 1.3 | 1.3 | 2.2 | 1.3 | 1.1 | 1.0 |
| Water | 2.5 | 2.5 | 2.5 | 2.5 | 2.5 | 1.4 | 5.9 | 2.0 | 1.7 | 1.6 |
| Acetone | 331 | 331 | 331 | 331 | 331 | 188 | 783 | 265 | 172 | 135 |
| Acid-cleavage conditions | | | | | | | | | | |
| Reaction temperature (°C.) | 67 | 67 | 67 | 67 | 67 | 72 | 60 | 70 | 71 | 71 |
| Residence time (minutes) | 5 | 5 | 5 | 5 | 5 | 5 | 5 | 5 | 5 | 5 |
| Composition of the acid-cleavage product (parts by weight) | | | | | | | | | | |
| Resorcinol | 66 | 66 | 66 | 66 | 66 | 59 | 68 | 64 | 64 | 60 |
| iso-Propylphenol | 9 | 9 | 9 | 9 | 9 | 9 | 9 | 9 | 9 | 9 |
| Toluene | 93 | 93 | 93 | 93 | 93 | 237 | 93 | 160 | 160 | 160 |
| Acetone | 426 | 426 | 426 | 426 | 426 | 282 | 877 | 359 | 266 | 229 |
| Water | 6.7 | 6.7 | 6.7 | 6.7 | 6.7 | 5.6 | 11.3 | 6.2 | 5.3 | 5.4 |
| Sulfuric acid | 1.3 | 1.3 | 1.3 | 1.3 | 1.3 | 1.3 | 2.2 | 1.3 | 1.1 | 1.0 |
| Other organic compounds | 70 | 70 | 70 | 70 | 70 | 77 | 67 | 71 | 71 | 75 |
| Toluene/acetone weight ratio at the time of cleavage | 0.22 | 0.22 | 0.22 | 0.22 | 0.22 | 0.84 | 0.11 | 0.45 | 0.60 | 0.70 |

| Example (Ex.) or Comparative Example (CEx.) | Ex. 5 | CEx. 7 | Ex. 6 | Ex. 7 | Ex. 8 | CEx. 8 | Ex. 9 | CEx. 9 | CEx. 10 |
|---|---|---|---|---|---|---|---|---|---|
| Composition of the starting material (parts by weight) | | | | | | | | | |
| m-DHP | 174 | 174 | 174 | 174 | 174 | 174 | 174 | 174 | 174 |
| m-MHP | 14 | 14 | 14 | 14 | 14 | 14 | 14 | 14 | 14 |
| m-HHP | 7 | 7 | 7 | 7 | 7 | 7 | 7 | 7 | 7 |
| Toluene | 160 | 160 | 160 | 160 | 160 | 160 | 160 | 160 | 0 (acetone 160) |
| Other organic compounds | 47 | 47 | 47 | 47 | 47 | 47 | 47 | 47 | 47 |
| Water | 1.5 | 1.5 | 1.5 | 1.5 | 1.5 | 1.5 | 1.5 | 1.5 | 0 |
| Catalyst solution (parts by weight) | | | | | | | | | |
| Sulfuric acid | 1.3 | 1.3 | 1.3 | 1.3 | 1.3 | 1.3 | 1.3 | 1.3 | 1.1 |
| Water | 2.0 | 2.0 | 2.0 | 2.0 | 2.0 | 2.0 | 2.0 | 2.0 | 1.7 |

TABLE 1-continued

| | | | | | | | | | |
|---|---|---|---|---|---|---|---|---|---|
| Acetone | 265 | 265 | 265 | 265 | 265 | 265 | 265 | 265 | 172 |
| Acid-cleavage conditions | | | | | | | | | |
| Reaction temperature (°C.) | 70 | 70 | 70 | 70 | 70 | 70 | 70 | 70 | 57 |
| Residence time (minutes) | 5 | 5 | 5 | 5 | 5 | 5 | 5 | 5 | 5 |
| Composition of the acid-cleavage product (parts by weight) | | | | | | | | | |
| Resorcinol | 64 | 64 | 64 | 64 | 64 | 64 | 64 | 64 | 67 |
| iso-Propylphenol | 9 | 9 | 9 | 9 | 9 | 9 | 9 | 9 | 9 |
| Toluene | 160 | 160 | 160 | 160 | 160 | 160 | 160 | 160 | — |
| Acetone | 359 | 359 | 359 | 359 | 359 | 359 | 359 | 359 | 428 |
| Water | 6.2 | 6.2 | 6.2 | 6.2 | 6.2 | 6.2 | 6.2 | 6.2 | 4.0 |
| Sulfuric acid | 1.3 | 1.3 | 1.3 | 1.3 | 1.3 | 1.3 | 1.3 | 1.3 | 1.1 |
| Other organic compounds | 71 | 71 | 71 | 71 | 71 | 71 | 71 | 71 | 6.8 |
| Toluene/acetone weight ratio at the time of cleavage | 0.45 | 0.45 | 0.45 | 0.45 | 0.45 | 0.45 | 0.45 | 0.45 | 0 |

TABLE 2

| Example (Ex.) or Comparative Example (CEx.) | Ex. 1 | CEx. 1 | CEx. 2 | CEx. 3 | CEx. 4 | CEx. 5 | Ex. 2 | Ex. 3 | Ex. 4 | CEx. 6 |
|---|---|---|---|---|---|---|---|---|---|---|
| Conditions for neutralization and extraction | | | | | | | | | | |
| Toluene added (parts by weight) | 258 | 0 | 258 | 258 | 101 | 0 | 652 | 145 | 26 | 0 |
| 20% aqueous Na₂SO₄ added (parts by weight) | 940 | 940 | 940 | 940 | 940 | 940 | 1785 | 826 | 712 | 665 |
| 25% aqueous NaOH added (parts by weight) | 4.4 | 4.4 | 6.6 | 5.5 | 4.4 | 4.4 | 3.7 | 4.9 | 3.8 | 3.5 |
| Temperature (°C.) | 50 | 50 | 50 | 50 | 50 | 50 | 50 | 50 | 50 | 50 |
| Residence time (minutes) | 30 | 30 | 30 | 30 | 30 | 30 | 30 | 30 | 30 | 30 |
| Toluene/acetone weight ratio at the time of extraction | 0.82 | 0.22 | 0.82 | 0.82 | 0.46 | 0.84 | 0.85 | 0.85 | 0.70 | 0.70 |
| pH of the solvent layer | 3.3 | 3.3 | 5.5 | 4.5 | 3.3 | 3.2 | 3.0 | 3.6 | 3.4 | 3.4 |
| Concentration of Na in the solvent layer (ppm) | 10 | 120 | 30 | 20 | 60 | 8 | 5 | 8 | 12 | 12 |
| Concentration of water in the solvent layer (%) | 6.6 | 18.5 | 6.6 | 6.6 | 12.5 | 5.6 | 5.6 | 5.7 | 6.5 | 6.5 |
| Total ratio of recovery of resorcinol based on m-DHP (%) | 86 | 88 | 75 | 78 | 87 | 76 | 88 | 84 | 84 | 77 |

| Example (Ex.) or Comparative Example (CEx.) | Ex. 5 | CEx. 7 | Ex. 6 | Ex. 7 | Ex. 8 | CEx. 8 | Ex. 9 | CEx. 9 | CEx. 10 |
|---|---|---|---|---|---|---|---|---|---|
| Conditions for neutralization and extraction | | | | | | | | | |
| Toluene added (parts by weight) | 55 | 20 | 91 | 199 | 139 | 270 | 91 | 91 | 0 |
| 20% aqueous Na₂SO₄ added (parts by weight) | 735 | 699 | 767 | 880 | 921 | 952 | 767 | 767 | 712 |
| 25% aqueous NaOH added (parts by weight) | 4.9 | 4.9 | 4.9 | 4.9 | 4.9 | 4.9 | 4.8 | 4.7 | 3.8 |
| Temperature (°C.) | 50 | 50 | 50 | 50 | 50 | 50 | 50 | 50 | 50 |
| Residence time (minutes) | 30 | 30 | 30 | 30 | 30 | 30 | 30 | 30 | 30 |
| Toluene/acetone weight ratio at the time of extraction | 0.60 | 0.50 | 0.70 | 1.00 | 1.10 | 1.20 | 0.70 | 0.70 | 0 |
| pH of the solvent layer | 3.5 | 3.3 | 3.5 | 3.6 | 3.5 | 3.7 | 2.5 | 1.5 | 3.0 |
| Concentration of Na in the solvent layer (ppm) | 15 | 55 | 12 | 8 | 7 | 4 | 10 | 8 | 200 |
| Concentration of water in the solvent layer (%) | 5.7 | 11.5 | 6.5 | 5.2 | 4.5 | 4.0 | 6.5 | 6.5 | 28.5 |
| Total ratio of recovery of resorcinol based on m-DHP (%) | 85 | 86 | 86 | 84 | 82 | 75 | 85 | 73 | 87 |

What we claim is:

1. In a process for producing resorcinol, which comprises cleaving m-diisopropylbenzene dihydroperoxide in the presence of a water-soluble acid catalyst in a mixed solvent consisting of toluene and acetone, treating the resulting acid cleavage product containing resorcinol with an aqueous solution of a neutral salt selected from the group consisting of sodium sulfate, potassium sulfate, sodium chloride and sodium phosphate under acidic conditions, separating the solvent layer containing resorcinol from the aqueous layer, and recovering resorcinol from the separated solvent layer; the improvement wherein (i) the acid cleavage is carried out while maintaining the weight ratio of toluene to acetone at less than 0.6, and at a time after formation of the acid cleavage product but before the treatment of the cleavage product with the aqueous solution of the neutral salt, the amount of toluene in the mixed solvent is adjusted so that the weight ratio of toluene to acetone in the product is from 0.6 to 1.1, and (ii) the acidic conditions are selected such that the pH of the solvent layer containing resorcinol is 2.5 to 4.

2. The process of claim 1 wherein the weight ratio of toluene to acetone in the acid cleavage step is from 0.05 to 0.55, and the amount of toluene in the mixed solvent is adjusted so that the weight ratio of toluene to acetone in the cleavage product is from 0.65 to 1.1.

3. The process of claim 1 wherein the m-diisopropylbenzene dihydroperoxide is a product of liquid-phase oxidation of m-diisopropylbenzene and/or m-diisopropylbenzene monohydroperoxide with molecular oxygen.

4. A process for producing resorcinol which comprises (a) cleaving m-diisopropylbenzene dihydroperoxide in the presence of a water-soluble acid catalyst in a mixed solvent consisting of an aromatic hydrocarbon and acetone, wherein the aromatic hydrocarbon is benzene, toluene, xylene, ethylbenzene, cumene, pseudocumene, cymene, diethylbenzene or m-diisopropylbenzene, while maintaining the weight ratio of aromatic hydrocarbon to acetone during the acid cleavage reaction at less than 0.6, (b) adjusting the aromatic hydrocarbon/acetone weight ratio after the acid cleavage reaction is completed to from 0.6 to 1.1, (c) treating the resulting acid cleavage product containing resorcinol, acid catalyst and said mixed solvent with an aqueous solution of a neutral salt selected from the group consisting of sodium sulfate, potassium sulfate, sodium chloride and sodium phosphate, under acidic conditions, to thereby form an aqueous layer containing said acid catalyst, and a solvent layer containing resorcinol, said acidic conditions being such that the pH of said solvent layer is from 2.5 to 4, (d) separating the solvent layer from the aqueous layer, and (e) recovering resorcinol from the separated solvent layer.

5. The process of claim 4 wherein in step (a) the weight ratio of the aromatic hydrocarbon to acetone is from 0.05 to 0.55 and in step (b) the weight ratio of aromatic hydrocarbon to acetone is adjusted to 0.65 to 1.1.

6. The process of claim 1 wherein in step (a), the amount of the mixed solvent is selected such that the concentration of resorcinol in the resulting reaction product is about 3 to about 20% by weight.

7. The process of claim 4 wherein in step (c), the acidic conditions are such that the pH of the solvent layer is from 2.5 to 3.5.

8. The process of claim 7 wherein in step (c), the resulting acid cleavage product from step (b) is treated with from about 0.3 to about 2 parts by volume of said aqueous solution containing from about 5 to about 30% by weight of said neutral salt, per volume of said resulting acid cleavage product.

9. The process of claim 5 or claim 7 wherein the aromatic hydrocarbon is toluene.

* * * * *